United States Patent [19]

de Koning et al.

[11] Patent Number: 5,075,398

[45] Date of Patent: Dec. 24, 1991

[54] BISMALEIMIDE-STYRENE COMPOUND-ACID COMPOUND-CONTAINING THERMOSETTING COMPOSITION

[75] Inventors: Adrianus J. de Koning, Munstergeleen; Jacobus Loontjens, Meerssen, both of Netherlands

[73] Assignee: DSM Resins B.V., Zwolle, Netherlands

[21] Appl. No.: 434,501

[22] Filed: Nov. 13, 1989

Related U.S. Application Data

[63] Continuation of Ser. No. 138,569, Dec. 28, 1987, abandoned, which is a continuation of Ser. No. 882,137, Jul. 2, 1986, abandoned, which is a continuation-in-part of Ser. No. 547,582, Nov. 1, 1983, abandoned.

[30] Foreign Application Priority Data

Nov. 6, 1982 [NL] Netherlands ............... 8204305
Sep. 20, 1983 [NL] Netherlands ............... 8303229

[51] Int. Cl.$^5$ ........................... C08F 222/40
[52] U.S. Cl. ..................... 526/262; 526/216; 528/322
[58] Field of Search ............. 526/262, 216; 528/322

[56] References Cited

U.S. PATENT DOCUMENTS

| | | | |
|---|---|---|---|
| 4,035,345 | 7/1977 | Dueloux et al. | 260/78 |
| 4,100,400 | 7/1978 | Callahan et al. | 235/92 |
| 4,277,582 | 7/1981 | Mueller et al. | 525/421 |
| 4,298,720 | 11/1981 | Yamazaki et al. | 526/262 |
| 4,323,662 | 4/1982 | Oba et al. | 525/261 |

FOREIGN PATENT DOCUMENTS 2010866 7/1979 United Kingdom .

*Primary Examiner*—Harold D. Anderson
*Attorney, Agent, or Firm*—Cushman, Darby & Cushman

[57] ABSTRACT

Thermosetting compositions consist of a homogeneous mixture of an ethylenically unsaturated compound, a bismaleimide compound or a bismaleimide containing composition and an acid compound, with optionally further copolymerizable compounds and usual additives. The thermosetting composition are useful as a coating resin, a laminating resin or for the manufacture of shaped articles.

14 Claims, No Drawings

BISMALEIMIDE-STYRENE COMPOUND-ACID COMPOUND-CONTAINING THERMOSETTING COMPOSITION

This is a continuation of application Ser. No. 07/138,569, filed Dec. 28, 1987, which was abandoned upon the filing hereof, which in turn is a continuation of Ser. No. 06/882,137, filed July 2, 1986, then abandoned, which is a continuation-in-part of Ser. No. 06/547,582, filed Nov. 1, 1983, now abandoned.

The invention relates to thermosetting compositions, and to polymers and objects obtained through curing of these, in which bismaleimide is processed. It is known to employ bismaleimides as a monomer or comonomer in compositions that are cured thermally, through an addition reaction or via radicals. The disadvantage of bismaleimides is that they are soluble in few other copolymerizable compounds. Solutions have been prepared of bismaleimides in, for instance, N-vinyl pyrrolidone, but such products have the disadvantage that the comonomer is expensive and renders the polymers obtained sensitive to water. It has been found to be impossible to dissolve more than 10 wt. % of a bismaleimide in styrene. This is a disadvantage, because styrene is a monomer that can easily be polymerized, is inexpensive and, moreover, is not sensitive to hydrolysis. The object of the invention is the preparation of compositions and copolymers in which both styrene or another copolymerizable compound and a substantial amount of a bismaleimide are processed. The invention provides a homogenous composition containing at least one bismaleimide having the formula

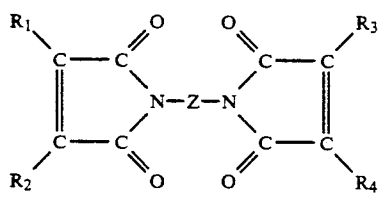

wherein $R_1$-$R_4$ each denote either an aliphatic, cycloaliphatic or aromatic group containing 1-12 carbon atoms, a hydrogen atom or a halogen atom, or where $R_1$ with $R_2$ and/or $R_3$ with $R_4$ form a ring system with at least one polymerizable C—C bond, and Z denotes an organic, bivalent group, the composition consisting of a homogeneous mixture of A. an ethylenically unsaturated compound, B. a bismaleimide compound or a bismaleimide-containing composition in such a quantity that the molar ratio between the bismaleimide and the ethylenically unsaturated compound is between 0.05:1 and 1:1, C. an acid compound in an effective amount of at least 1 wt. %, calculated in relation to the weights of A and B together, D. optionally, one or more other polymerizable monomer or polymer compounds, E. optionally, one or more usual additives, such as inhibitors, curing catalysts, fillers, reinforcing agents, pigments, etc.

It is found that in the presence of an acid, particularly a polymerizable acid, bismaleimide and bismaleimide containing compositions are better soluble in styrene. The cured products have a good chemical resistance, a high maximum processing temperature and a low combustibility.

Bismaleimides are known compounds. They can be synthesized using the processes described in U.S. Pat. No. 3,018,290 and GB-A 1,137,592. After separation of the solvent, by pouring the reaction mixture in water and filtration or by evaporation, the bismaleimides can be isolated with a purity of more than 90%. Bismaleimide compounds can also be prepared as a composition containing monomaleimide compounds, as disclosed in copending Netherlands patent application No. 8303229, which corresponds to U.S. application Ser. No. 650,080, filed Sept. 13, 1984, now U.S. Pat. No. 4,582,883, the disclosure of which is herewith incorporated by reference.

The bismaleimides to be employed in the invention comprise compounds having the formula I, where $R_1$-$R_4$ each and independently of each other denote a hydrogen atom, a halogen atom or an aliphatic, cycloaliphatic or aromatic group containing 1-12 carbon atoms, or where $R_1$ and $R_2$ together and/or $R_3$ and $R_4$ together form a ring system with at least one polymerizable carbon-carbon bond, and Z denotes a bivalent group. By preference, $R_1$-$R_4$ each are a hydrogen, chlorine, methyl or ethyl group, in particular a hydrogen atom. The Z group may be an aliphatic, cycloaliphatic, aromatic or heterocyclic group and generally contains 2-25 carbon atoms. When Z is an aliphatic group, it preferably contains 2-6 carbon atoms. Z preferably is an aromatic group, in particular a meta- or para-phenylene group or a group of the formula

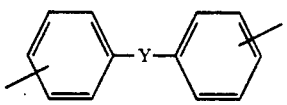

where Y denotes a —$CH_2$—, a —$C(CH_3)_2$—, an —O— or an —$SO_2$-group. Suitable compounds are in particular:

N,N'-ethylene-bismaleimide
N,N'-hexamethylene-bismaleimide
N,N'-m-phenylene-bismaleimide
N,N'-p-phenylene-bismaleimide
N,N'-4,4'-diphenylmethane-bismaleimide
N,N'-4,4'-diphenylether-bismaleimide
N,N'-4,4'-diphenylsulfone-bismaleimide
N,N'-4,4'-dicyclohexylmethane-bismaleimide
N,N'-pyridinediyl-(2,6)-bismaleimide
N,N'-4,4'(3,5 diphenylpyridine)-bismaleimide
N,N'-α,α'-4,4'-dimethylene cyclohexane-bismaleimide
N,N'-m-xylylene-bismaleimide
N,N'-p-xylylene-bismaleimide
N,N'-4,4'-(2.2. diphenylpropane)-bismaleimide
N,N'-3,5-(1.2.4 triazol)-bismaleimide
N,N'-4,4'-diphenylmethane-biscitraconimide.

The ethylenically unsaturated compound employed in the present invention is selected from the group consisting of α-methyl styrene, para-methyl styrene, chlorostyrene, divinyl benzene and vinyl toluene. Ethylenically unsaturated monomers that are known to inhibit, to a certain level, the radical polymerization are excluded from the present invention. Examples of such ethylenically unsaturated compounds are hydroxy styrene and amino styrene.

The molar ratio between bismaleimide and ethylenically unsaturated compound, preferably a vinyl aromatic compound, generally is between 0.05:1 and 1:1 and preferably between 0.2:1 to 0.8:1. The optimum appears to lie at a ratio of between 0.35:1 and 0.60:1. As the vinyl aromatic compound, by preference styrene is used.

As the acid compound, by preference carboxylic acid compounds or corresponding acid anhydrides with in general 2-25 carbon atoms are used. They are employed to form a homogenous solution together with the ethylenically unsaturated compound and the bismaleimide compound/composition. Though polycarboxylic acids can be employed, mostly a monocarboxylic acid containing 2-12 carbon atoms, a dicarboxylic acid semi-ester, a dicarboxylic acid or a dicarboxylic acid anhydride will be used. By preference, an unsaturated, polymerizable, acid compound containing at least 3 C atoms is employed. These compounds are capable of copolymerization with the (bis)maleimide compound/composition and/or the ethylenically unsaturated compound, though the formation of some amount of homopolymer is also possible. Examples are acetic acid, acetic acid anhydride, trichloro-acetic acid, benzoic acid, acrylic acid, crotonic acid, cinnamic acid, methacrylic acid, mono-ethylmaleate, mono-2-ethylhexylmaleate, monobutylfumarate, maleic acid, fumaric acid, itaconic acid, citraconic acid anhydride and maleic acid anhydride. The acid is employed in an amount that is at least effective, i.e. enough to form a stable, homogenous solution with the bismaleimide and the vinyl aromatic compound. At least 1 wt. % relative to the bismaleimide and the vinyl aromatic is employed. The amount minimally required in part depends on the choice of the acid and the choice of the bismaleimide. In general, an amount of between 1 and 40 wt. % calculated in relation to bismaleimide plus vinyl aromatic is sufficient. By preference between 5 and 25 wt. % is employed. The most suitable acid compounds are acrylic acid, crotonic acid, maleic acid, fumaric acid and maleic acid anhydride.

It is also possible to add other (co)polymerizable compounds insofar as these do not bring about a phase separation. Unsaturated polyesters may be considered, and further compounds such as prepolymers of diallyl esters and ethers, for instance prepolymers of diallyl phthalate.

In general, such compounds are supplied in an amount of at most 100 wt. %, calculated in relation to the other unsaturated components A through C and, by preference in an amount of at most 50 wt. %.

Further, it is limitedly possible to add usual materials such as inhibitors, pigments, fillers, reinforcing agents, shrinkage controlling agents, etc. The term homogenous relates only to the polymerizable part of the composition. Examples of possible additives are glass fibres, carbon fibres, metal fibres, aramide fibres, lime, chalk, sand, silica, aluminum oxide hydrate, polybutadiene, polystyrene, polyethylene, polypropylene and polyacrylates. For curing a radical source is added. As such a hydroperoxide, a perester, a perketone or another compound suitable for curing of styrene copolymers can be used.

Curing takes place under the influence of radicals. Under such conditions, bismaleimides rapidly polymerize, so that the polymerization can be effected as well at a low temperature (less than 75° C.) as at an elevated temperature.

The compositions according to the invention can be used, inter alia, as casting resin, laminating resin or for the manufacture of objects.

The compositions according to the invention possess a combination of favorable properties. Before curing they are liquids, with a viscosity that generally is low at room temperature, that can well be employed for casting or impregnating. After curing at room temperature, preferably followed by after-curing at a higher temperature, for instance between 100° C. and 250° C., products are obtained that possess good mechanical and physical properties.

The invention will be elucidated on the bases of the following examples without being limited to the embodiments described therein.

EXAMPLE I

Into a reaction vessel provided with a stirrer and placed in a bath that was kept at a temperature of 80°-100° C. by means of a thermostat, 50 g of N,N'-4,4'-diphenylmethane-bismaleimide, 35 g styrene, 15 g acrylic and 0.04 g benzoquinone were introduced. The mixture was stirred for 15 minutes, upon which it had the form of a clear, transparent, reddish solution with a viscosity of less than 2P. The solution remained homogenous even after cooling to 15°-20° C. After degassing of the solution and addition of 2% methylethylketone peroxide (50% solution in dimethylphthalate), the solution was cast into a rectangular mould (127×75×4 mm). Curing took place at room temperature; the gelation time was about 3 minutes. After 24 hours the cured sheet obtained further was heated at a temperature of 80° C. for 24 hours and at a temperature of 110° C. for another 24 hours. The properties of the products obtained by casting are summarized in Table A.

EXAMPLE II

The process of Example I was repeated, the mixture used now being composed of 25 g N,N'-4,4'-diphenylmethane-bismaleimide, 25 g N,N'-4,4'-diphenylmethane-bis-citraconimide, 35 g styrene, 15 g acrylic acid and 0.04 g benzoquinone. The properties of the castings obtained under the circumstances described in Example I are summarized in Table A.

EXAMPLE III

The process of Example I is repeated, but now using a mixture consisting of 34 g N,N'-4,4'-diphenylmethane-bismaleimide, 22 g N,N'-hexamethylene-bismaleimide, 34 g styrene, 10 g maleic acid anhydride and 0.04 g benzoquinone. The properties of the cast products obtained with this resin in accordance with the instructions of Example I are mentioned in Table A.

EXAMPLE IV

Analogously with the process used in Example I a homogenous mixture is obtained starting from 50 g N,N'-4,4'-diphenylmethane-bismaleimide, 30 g styrene, 10 g acrylic acid and 10 g diallylphthalate. As inhibitor use was made of 0.04 wt. % benzoquinone. The properties of the cured products as obtained by the process of Example I are shown in Table A.

EXAMPLE V

Mixing of 50 g N,N'-4,4'-diphenylmethane-bismaleimide, 30 g styrene, 10 g acrylic acid, 10 g diallyl maleate and 0.04 g benzoquinone according to the instructions of Example I yields a dark red, liquid composition. The properties of the cast products are represented in Table A.

EXAMPLE VI 100 g of 4,4'diaminodiphenylmethane, dissolved in 300 ml of acetone are added slowly to a solution of 100 g of maleic anhydride in 700 ml acetone at room temperature.

There results a substantially quantitative precipitate of the corresponding dimaleamic acid. At a temperature of 60° C. 150 g of acetic anhydride and 1.5 g of 1,4-diaza-bicyclo-(2,2,2) octane (DABCO) are added.

The end of the reaction is indicated by the disappearance of the dimaleamic acid precipitate. After removing the solvent, acetic acid and acetic anhydride under vacuum of 0.1 mm Hg at 80°-100° C., there is obtained in almost quantitative yield, a mixture consisting of 70% of N,N',4,4'-diphenylmethane bismaleimide, 25% of 4-acetylaminophenyl-4'-maleimidophenyl methane and about 5% of maleic anhydride.

50 g of this mixture are stirred with 25 g of styrene, 12 g of diallyl phthalate and 13 g of acrylic acid, in the manner described in example I, and the obtained composition was cast and cured following the method of example I.

The properties of the case products are represented in Table A.

EXAMPLE VII

To 50 g N,N'-4,4'-diphenylmethane bismaleimide, 5 g acrylic acid, 25 g styrene and 0.03 g benzoquinone were added. These ingredients were thoroughly stirred for 30 minutes at 100° C. A homogenous resin was obtained, which remained homogenous after cooling to room temperature. This resin has a good compatibility with E-glass and is suitabe for building up glass fibre reinforced products.

TABLE A

| Properties | Example I | Example II | Example III | Example IV | Example V | Example VI |
|---|---|---|---|---|---|---|
| E-modulus from bending test (ASTM D 790) in N/mm² | 4290 | 4470 | 4240 | 3160 | 3280 | 2900 |
| Maximum stress (ASTM D 790) in N/mm² | 51 | 39 | 42 | 94 | 63 | 95 |
| Maximum strain (ASTM D 790) in % | 1.2 | 0.9 | 1.0 | 3.1 | 1.9 | 3.9 |
| HDT (ASTM 648) IN °C. | 130 | — | — | 138 | 141 | 230 |
| Barcol hardness (GYZJ 934-1) | 55 | 50 | 50 | 45 | 45 | 53 |

What is claimed is:

1. A homogeneous, curable composition capable of radial polymerization containing an ethylenically unsaturated compound selected from the group consisting of styrene, α-methylstyrene, p-methylstyrene, chlorostyrene, divinylbenzene and vinyl toluene, which composition comprises:

(a) at least one bismaleimide having the formula

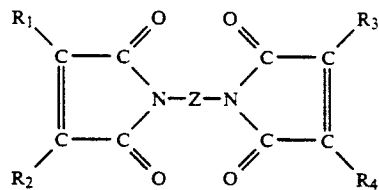

wherein $R_1$–$R_4$ each independently represents a member selected from the group consisting of hydrogen; an aliphatic, cycloaliphatic or aromatic group, containing 1–12 carbon atoms; and halogen, one or both of the pairs $R_1$ and $R_2$, and $R_3$ and $R_4$, form a ring system together with the —C=C— group to which they are attached; and Z represents a bivalent group;

(b) said ethylenically unsaturated compound; and (c) an acid compound selected from the group consisting of a carboxylic acid and carboxylic acid anhydride, present in an amount of at least 1 weight percent based on the total weight of (a) and (b), wherein the molar ratio of said bismaleimide (a) to said ethylenically unsaturated compound (b) is between 0.05;1 and 1:1.

2. The homogeneous, curable composition of claim 1 wherein the molar ratio of said bismaleimide to said ethylenically unsaturated compound ranges from 0.2:1 to 0.8:1.

3. The homogeneous, curable composition of claim 1 wherein the molar ratio of said bismaleimide to said ethylenically unsaturated compound ranges from 0.35:1 to 0.06:1.

4. The homogeneous, curable composition of claim 1 wherein said acid compounds is a polymerizable carboxylic acid containing 3–12 carbon atoms, said carboxylic acid being selected from the group consisting of a monocarboxylic acid, a dicarboxylic acid and dicarboxylic acid anhydride.

5. The homogeneous, curable composition of claim 1 wherein said acid compound is selected from the group consisting of maleic acid, fumaric, maleic acid anhydride, crotonic acid, cinnamic acid and acrylic acid.

6. The homogenous, curable composition of claim 1 wherein said acid compound is present in an amount between 1 and 40 weight percent based on the total weight of (a) and (b).

7. A homogenous, curable composition consisting essentially of (a) a bimaleimide selected from the group consisting of
  N,N'-ethylene-bismaleimide,
  N,N'-hexamethylene-bismaleimide,
  N,N'-m-phenylene-bismaleimide,
  N,N'-p-phenylene-bismaleimide,
  N,N'-4,4'-diphenylmethane-bismaleimide,
  N,N'-4,4'-diphenylether-bismaleimide,
  N,N'-4,4'-diphenylsulfone-bismaleimide,
  N,N'-4,4'-dicyclohexylmethane-bismaleimide,
  N,N'-pyridinediyl-(2,6)-bismaleimide,
  N,N'-4,4'(3,5-diphenyl pyridine)-bismaleimide,
  N,N'-α,α'-4,4'-dimethylene cyclohexane-bismaleimide,
  N,N'-m-xylylene-bismaleimide,
  N,N'-p-xylylene-bismaleimide,
  N,N'-4,4'-(2.2-diphenyl propane)-bismaleimide,
  N,N'-3,5-(1.2.4 triazol)-bismaleimide, N,N'-4,4'-diphenylmethane-biscitraconimide, and (b) an ethylenically unsaturated compound selected from the group consisting of styrene, α-methyl styrene, paramethyl styrene, chlorostyrene, divinyl benzene and vinyl toluene;

(c) an acid compound selected from the group consisting of acid, acrylic acid, crotonic acid, cinnamic acid, methacrylic acid, mono-ethyl maleate, mono-2-ethylhexyl maleate, mono-butyl fumrate, maleic acid, fumaric acid, itaconic acid, citraconic acid anhydride and maleic acid anhydride, the molar ratio of said bismaleimide to said ethylenically unsaturated compound ranging between 0.05:1 to 1:1.

8. A homogeneous, curable composition capable of radical polymerization containing an ethylenically unsaturated compound selected from the group consisting of styrene, α-methylstyrene, p-methylstyrene, chlorostyrene, divinylbenzene and vinyl toluene, which composition comprises:

(a) at least one bismaleimide having the formula

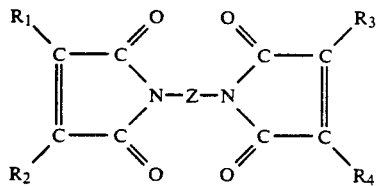

wherein $R_1$-$R_4$ each independently represents a member selected from the group consisting of hydrogen; an aliphatic, cycloaliphatic or aromatic group, containing 1-12 carbon atoms; and halogen, one or both of the pairs $R_1$ and $R_2$, and $R_3$ and $R_4$, form a ring system together with the —C=C— group to which they are attached; and Z represents a bivalent, cycloaliphatic, aromatic or heterocyclic group of 2-25 carbon atoms or an aliphatic group of 2-6 carbon atoms;

(b) said ethylenically unsaturated compound; and (c) an acid compound selected from the group consisting of a carboxylic acid and carboxylic acid anyhydride, present in an amount of at least 1 weight percent based on the total weight of (a) and (b), wherein the molar ratio of said bismaleimide (a) to said ethylenically unsaturated compound (b) is between 0.05:1 and 1:1.

9. The homogeneous, curable composition of claim 8 wherein the molar ratio of said bismaleimide to said ethylenically unsaturated compound ranges from 0.2:1 to 0.8:1.

10. The homogeneous, curable composition of claim 8 wherein the molar ratio of said bismaleimide to said ethylenically unsaturated compound ranges from 0.35:1 to 0.06:1.

11. The homogeneous, curable composition of claim 8 wherein said acid compound is a polymerizable carboxylic acid containing 3-12 carbon atoms, said carboxylic acid being selected from the group consisting of a monocarboxylic acid, a dicarboxylic acid and a dicarboxylic acid anhydride.

12. The homogeneous, curable composition of claim 8 wherein said acid compound is selected from the group consisting of maleic acid, fumaric, maleic acid anhydride, crotonic acid, cinnamic acid and acrylic acid.

13. The homogeneous, curable composition of claim 8 wherein said acid compound is present in an amount between 1 and 40 weight percent based on the total weight of (a) and (b).

14. A homogeneous, curable composition capable of radical polymerization containing an ethylenically unsaturated compound selected from the group consisting of styrene, α-methylstyrene, p-methylstyrene, chlorostyrene, divinylbenzene and vinyl toluene, which composition comprises:

(a) at least one bismaleimide having the formula

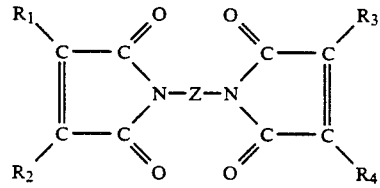

wherein $R_1$-$R_4$ each independently represents a member selected from the group consisting of hydrogen; an aliphatic, cycloaliphatic or aromatic group, containing 1-12 carbon atoms; and halogen, one or both of the pairs $R_1$ and $R_2$, and $R_3$ and $R_4$, form a ring system together with the —C=C— group to which they are attached; and Z represents a group of 2-25 carbon atoms or an aliphatic group of 2 carbon atoms or 6 carbon atoms;

(b) said ethylenically unsaturated compound; and (c) an acid compound selected from the group consisting of a carboxylic acid and carboxylic acid anhydride, present in an amount of at least 1 weight percent based on the total weight of (a) and (b), wherein the molar ratio of said bismaleimide (a) to said ethylenically unsaturated compound (b) is between 0.05:1 and 1:1.

* * * * *